May 8, 1973 F. W. ANDERSON Plant Pat. 3,330
NECTARINE TREE
Filed Sept. 27, 1971
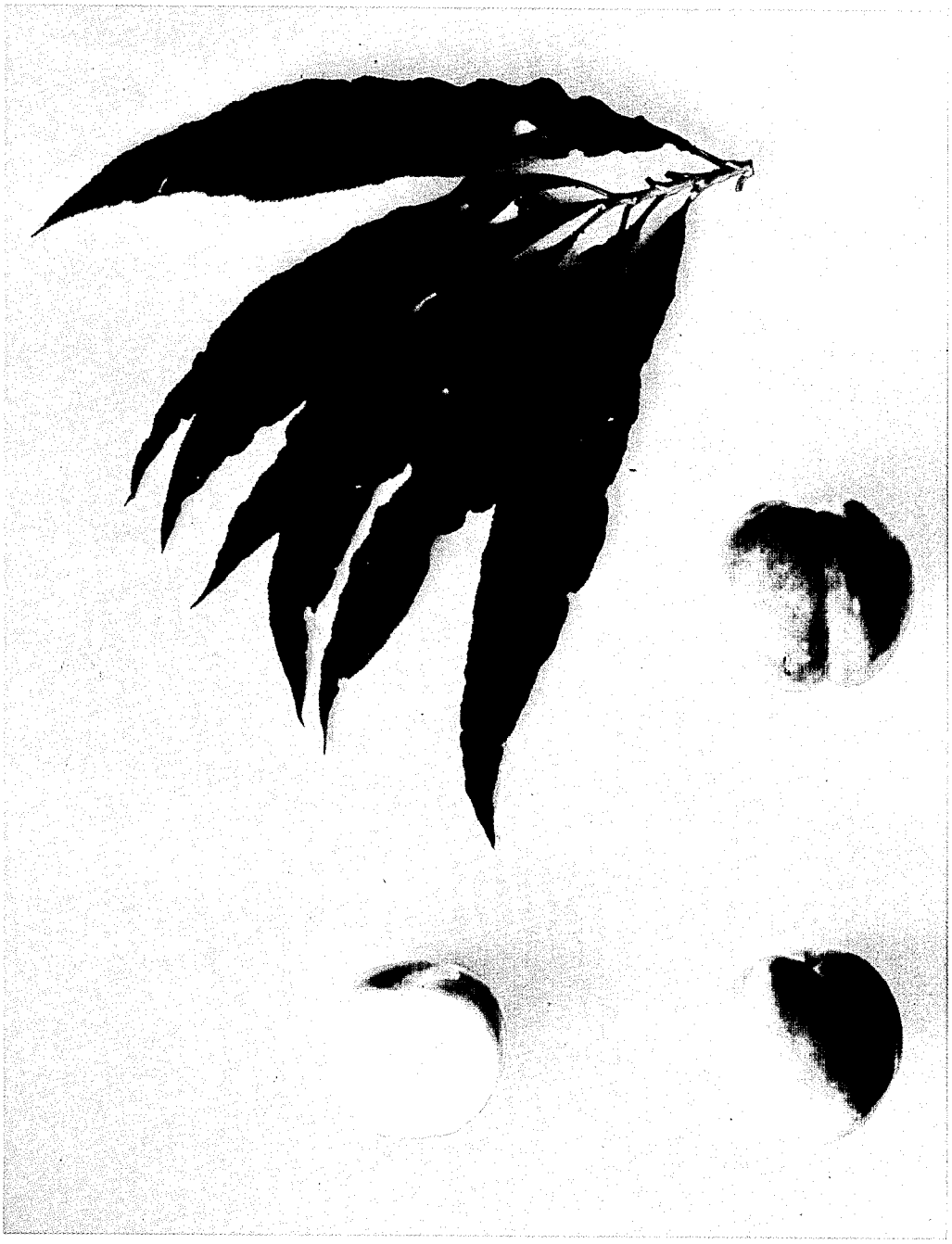
INVENTOR
Frederic W. Anderson
BY
Webster & Webster
ATTORNEYS United States Patent Office Plant Pat. 3,330
Patented May 8, 1973

3,330

NECTARINE TREE

Frederic W. Anderson, Merced, Calif., assignor to Stark Bro's Nurseries and Orchards Co., Louisiana, Mo.

Filed Sept. 27, 1971, Ser. No. 184,060
Int. Cl. A01h 5/03
U.S. Cl. Plt.—41 1 Claim

ABSTRACT OF THE DISCLOSURE

A genetically dwarf nectarine tree, with short internodes, which is of medium size, very vigorous, spreading, dense, foliated with large lanceolate, acutely pointed leaves, flowered with self-fertile bloom, and is a regular and very productive bearer of uniform, symmetrical, medium size, globose fruit having yellow skin substantially overspread with red, and firm, crisp, yellow flesh with red at the surface of the pit cavity; the fruit—which is glossy—ripening about a month earlier than the Golden Prolific (United States Plant Patent No. 2,193), being clingstone instead of freestone, and having globose instead of reniform glands.

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

ORIGIN OF THE VARIETY

The present variety of nectarine tree was originated by me, in my experimental orchard located as aforesaid, as a cross between two unnamed nectarines (both unpatented) which bore yellow flesh fruit. In maturity, such cross evidenced the novel and distinct characteristics herein described, and I, therefore, selected it for asexual reproduction preparatory to ultimate commercial growing.

ASEXUAL REPRODUCTION OF THE VARIETY

I asexually reproduced the present variety of nectarine tree by top-working the same on mature orchard trees located in my said experimental orchard, and such reproductions were found to run true to the original tree in all respects.

SUMMARY OF THE VARIETY

The present variety of nectarine tree is a genetic dwarf with short internodes and is of medium size, very vigorous, spreading, dense, foliated with large lanceolate, acutely pointed leaves, flowered with self-fertile bloom, and is a regular and very productive bearer of uniform, symmetrical, medium size, globose fruit having yellow skin substantially overspread with red, and firm, crisp, yellow flesh with red at the surface of the pit cavity; the fruit—which is glossy—ripening about a month earlier than the Golden Prolific, being clingstone instead of freestone, and having globose instead of reniform glands.

By virtue of its firm, crisp flesh, the fruit of the present variety—whose eating quality is such that it can compete in the market with fruit of varieties of tall-growing nectarine trees—also has good shipping quality and which permits of long distance shipping.

BRIEF DESCRIPTION OF THE DRAWING

The drawing is an illustration, by photographic reproduction in color, of leaves and fruit of the variety; one fruit having a portion cut away to expose the flesh.

DESCRIPTION OF THE VARIETY

The botanical details of this new and distinct variety of nectarine tree—with color definitions (except those in common color terms) referenced to Maerz and Paul Dictionary of Color—are as follows:

Tree:
- *Type.*—Dwarf, with short internodes.
- *Size.*—Medium.
- *Vigor.*—Very vigorous.
- *Growth.*—Spreading.
- *Density.*—Dense.
- *Production.*—Very productive.
- *Bearing.*—Regular bearer.

Trunk:
- *Size.*—Stocky.
- *Texture.*—Shaggy.

Branches:
- *Size.*—Stocky.
- *Texture.*—Medium.

Leaves:
- *Size.*—Large, average length—7", average width—1¼".
- *Form.*—Lanceolate, acutely pointed.
- *Color.*—Top side—dark green (24–L–10), under side—lighter green (23–J–8).
- *Margin.*—Crenate.
- *Petiole.*—Short.
- *Glands.*—Number and position—usually 2 at base of blade, globose.

Flower buds:
- *Length.*—Medium.

Flowers:
- *Blooming period.*—Medium, as compared with other varieties.
- *Date of first bloom.*—Mar. 3, 1970.
- *Date of full bloom.*—Mar. 15, 1970.
- *Size.*—Large.
- *Fertility.*—Self-fertile, with red anthers before dehiscence.

Fruit:
- *Maturity when described.*—Eating ripe—July 20, 1970.
- *Date of first picking.*—July 14, 1970.
- *Date of last picking.*—July 24, 1970.
- *Size.*—Uniform, medium, average diameter axially—2⅜", average transversely in suture plane—2¼".
- *Form.*—Uniform, symmetrical, globose.
- *Suture.*—Distinct but shallow; extends from base to beyond apex over entire circumference; marked depression beyond pistil point.
- *Base.*—Truncate.
- *Apex.*—Short, depressed.

Skin:
- *Thickness.*—Medium.
- *Tendency to crack.*—None.
- *Down.*—Wanting.
- *Color.*—Yellow (10–L–6) substantially overspread with red (6–L–5) shading slightly darker on sunny side. Glossy.

Flesh:
- *Texture.*—Firm, crisp.
- *Fibers.*—Few.
- *Ripens.*—Evenly.
- *Flavor.*—Subacid to mild.
- *Eating quality.*—Fair to good.
- *Color.*—Yellow (11–L–5). Surface of pit cavity—Red (5–L–3).

Stone:
- *Type.*—Cling.
- *Size.*—Medium, average length—1¼", average breadth—1⅛", average thickness—¾".

*Tendency to split.*—Slight.

*Color.*—Garnet red (7–H–6).

Use: Market—local and long distance shipping.

Keeping quality: Medium.

Resistance to insects and diseases: No unusual susceptibilities noted.

Shipping quality: Good.

The nectarine tree and its fruit herein described may vary in slight detail due to climatic and soil conditions under whch the variety may be grown; the present description being of the variety as grown in the Central Valley of California.

I claim:

1. A new and distinct variety of genetically dwarf nectarine tree—substantially as illustrated and described—having short internodes, and which is of medium size, very vigorous, spreading, dense, foliated with large lanceolate, acutely pointed leaves, flowered with self-fertile bloom, and is a regular and very productive bearer of uniform, symmetrical, medium size, globose fruit having yellow skin substantially overspread with red, and firm, crisp, yellow flesh with red at the surface of the pit cavity; the fruit—which is glossy—ripening about a month earlier than the Golden Prolific, being clingstone instead of freestone, and having globose instead of reniform glands.

No references cited.

ROBERT BAGWILL, Primary Examiner